US011864735B2

(12) United States Patent
Begg et al.

(10) Patent No.: US 11,864,735 B2
(45) Date of Patent: Jan. 9, 2024

(54) CONTINUOUS FLOW ENDOSCOPE

(71) Applicant: COVIDIEN LP, Mansfield, MA (US)

(72) Inventors: Nikolai D. Begg, Wayland, MA (US); Dalia Leibowitz, White Plains, NY (US); Mireille Akilian, Somerville, MA (US)

(73) Assignee: Covidien LP, Mansfield, MA (US)

( * ) Notice: Subject to any disclaimer, the term of this patent is extended or adjusted under 35 U.S.C. 154(b) by 837 days.

(21) Appl. No.: 15/603,209

(22) Filed: May 23, 2017

(65) Prior Publication Data

US 2017/0340192 A1    Nov. 30, 2017

Related U.S. Application Data

(60) Provisional application No. 62/341,908, filed on May 26, 2016.

(51) Int. Cl.
    *A61B 1/015* (2006.01)
    *A61B 1/00* (2006.01)
    (Continued)

(52) U.S. Cl.
    CPC .......... *A61B 1/015* (2013.01); *A61B 1/00128* (2013.01); *A61B 1/00165* (2013.01);
    (Continued)

(58) Field of Classification Search
    CPC . A61B 1/015; A61B 1/00128; A61B 1/00165; A61B 1/018; A61B 1/3132;
    (Continued)

(56) References Cited

U.S. PATENT DOCUMENTS 1,585,934 A    5/1926  Muir
1,666,332 A    4/1928  Hirsch
(Continued)

FOREIGN PATENT DOCUMENTS

JP    105-285094 A    11/1993
JP    H06-181879 A     7/1994
WO       94-05200 A1   3/1994

OTHER PUBLICATIONS

Notification of Transmittal of the International Search Report and the Written Opinion of the Internatonal Searching Authority, or the Declaration issued in corresponding PCT application No. PCT/US2017/034302 dated Jul. 21, 2017.
(Continued)

*Primary Examiner* — Ryan N Henderson
(74) *Attorney, Agent, or Firm* — Carter, DeLuca & Farrell LLP

(57) ABSTRACT

A continuous flow endoscope device includes an elongated tubular member defining an interior, a first channel disposed within the interior of the elongated tubular member, a second channel disposed within the interior of the elongated tubular member, and an optics device disposed in a free space of the interior of the elongated tubular member. The second channel is configured to receive an instrument therein during a first portion of an operation. A lumen defined through the second channel is fluidly isolated from a lumen defined through the first channel. The free space of the interior of the elongated tubular member being a space within the interior of the elongated tubular member not occupied by either the first channel or the second channel.

11 Claims, 6 Drawing Sheets

(51) Int. Cl.
  *A61B 1/018* (2006.01)
  *A61B 1/313* (2006.01)
  *A61B 1/07* (2006.01)

(52) U.S. Cl.
  CPC ............ *A61B 1/018* (2013.01); *A61B 1/3132* (2013.01); *A61B 1/00167* (2013.01); *A61B 1/07* (2013.01)

(58) Field of Classification Search
  CPC ... A61B 1/00167; A61B 1/07; A61B 1/00071; A61B 1/00096; A61B 1/12; A61B 1/126; A61B 1/127; A61B 1/128; A61B 1/303; A61B 1/307; A61B 1/317; A61B 1/00094; A61B 17/320016; A61B 17/32002; A61B 2017/320024; A61B 2017/320028; A61B 2017/320032; A61M 39/22; A61M 39/24; A61M 39/223; A61M 2039/224; A61M 2039/2473; A61M 2039/248; A61M 2039/2486
  See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A * | 2/1974 | Storz ............... A61B 1/12 137/625.24 |
| 3,812,855 A | 5/1974 | Banko |
| 3,850,162 A | 11/1974 | Iglesias |
| 3,900,022 A | 8/1975 | Widran |
| 3,939,839 A | 2/1976 | Curtiss |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,423,727 A | 1/1984 | Widran et al. |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A * | 7/1991 | Meyer ............... A61B 1/12 600/105 |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,191,878 A | 3/1993 | Iida et al. |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,257,617 A | 11/1993 | Takahashi |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Takky et al. |
| 5,312,425 A | 5/1994 | Evans et al. |
| 5,312,430 A | 5/1994 | Rosenbluth et al. |
| 5,320,091 A * | 6/1994 | Grossi ............... A61B 1/00135 600/156 |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,411,513 A | 5/1995 | Ireland et al. |
| 5,425,376 A | 6/1995 | Banys et al. |
| 5,429,601 A | 7/1995 | Conley et al. |
| 5,443,476 A | 8/1995 | Shapiro |
| 5,449,356 A | 9/1995 | Walbrink et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Ili |
| 5,602,449 A | 2/1997 | Krause et al. |
| 5,603,332 A | 2/1997 | O'Connor |
| 5,630,798 A | 5/1997 | Beiser et al. |
| 5,637,075 A | 6/1997 | Kikawada |
| 5,649,547 A | 7/1997 | Ritchart et al. |
| 5,669,927 A | 9/1997 | Boebel et al. |

(56) References Cited

U.S. PATENT DOCUMENTS

| | | |
|---|---|---|
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,654 A | 8/1999 | Crawford |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A * | 2/2000 | Lovato ............... A61B 1/015 606/180 |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Tibner et al. |
| 6,132,369 A | 10/2000 | Takahashi |
| 6,132,448 A | 10/2000 | Perez et al. |
| 6,149,633 A | 11/2000 | Maaskamp |
| 6,156,049 A * | 12/2000 | Lovato ............... A61B 1/015 606/180 |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 * | 3/2002 | Grossi ............... A61B 18/24 600/128 |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,759 B2 * | 3/2004 | Muller ............... A61B 1/00135 600/129 |
| 6,712,773 B1 | 3/2004 | Viola |
| 6,808,505 B2 * | 10/2004 | Kadan ............... A61B 17/3421 604/27 |
| 6,837,847 B2 | 1/2005 | Ewers et al. |
| 7,025,720 B2 * | 4/2006 | Boebel ............... A61B 1/00163 600/105 |
| 7,025,732 B2 | 4/2006 | Thompson et al. |
| 7,150,713 B2 * | 12/2006 | Shener ............... A61B 1/00135 600/128 |
| 7,226,459 B2 | 6/2007 | Cesarini et al. |
| 7,249,602 B1 * | 7/2007 | Emanuel ............... A61B 1/12 606/15 |
| 7,510,563 B2 | 3/2009 | Cesarini et al. |
| 7,763,033 B2 | 7/2010 | Gruber et al. |
| 7,918,863 B2 * | 4/2011 | Nguyen ............... A61B 1/018 606/135 |
| 7,922,737 B1 | 4/2011 | Cesarini et al. |
| 8,061,359 B2 | 11/2011 | Emanuel |
| 8,062,214 B2 * | 11/2011 | Shener ............... A61B 1/015 600/105 |
| 8,905,920 B2 * | 12/2014 | Meloul ............... A61B 1/00137 600/106 |
| 9,072,431 B2 * | 7/2015 | Adams ............... A61B 1/015 |
| 9,155,453 B2 * | 10/2015 | Kumar ............... A61B 17/32002 |
| 9,155,454 B2 * | 10/2015 | Sahney ............... A61B 17/42 |
| 9,226,650 B2 | 1/2016 | Emanuel |
| 9,427,247 B2 * | 8/2016 | Emanuel ............... A61B 17/42 |
| 9,474,438 B2 * | 10/2016 | Fan ............... A61B 1/00128 |
| 10,251,539 B2 * | 4/2019 | Sahney ............... A61B 1/015 |
| 10,751,451 B2 * | 8/2020 | Klein ............... A61M 3/0229 |
| 10,786,142 B2 * | 9/2020 | Kiedrowski ............ A61B 1/307 |
| 2001/0039963 A1 | 11/2001 | Spear et al. |
| 2001/0047183 A1 | 11/2001 | Privitera et al. |
| 2002/0058859 A1 | 5/2002 | Brommersma |
| 2003/0050603 A1 * | 3/2003 | Todd ............... A61B 17/3421 604/164.02 |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2003/0125607 A1 * | 7/2003 | Boebel ............... A61B 1/00163 600/130 |
| 2003/0130565 A1 * | 7/2003 | Muller ............... A61B 1/00135 600/156 |
| 2004/0082915 A1 * | 4/2004 | Kadan ............... A61B 1/00105 604/164.04 |
| 2004/0204671 A1 | 10/2004 | Stubbs et al. |
| 2005/0043690 A1 | 2/2005 | Todd |
| 2005/0085692 A1 * | 4/2005 | Kiehn ............... A61B 1/00105 600/128 |
| 2005/0085695 A1 * | 4/2005 | Shener ............... A61B 1/00071 600/156 |
| 2006/0036132 A1 | 2/2006 | Renner et al. |
| 2006/0047185 A1 * | 3/2006 | Shener ............... A61B 1/015 600/156 |
| 2006/0241586 A1 | 10/2006 | Wilk |
| 2006/0293560 A1 * | 12/2006 | Nguyen ............... A61F 6/06 600/104 |
| 2008/0015621 A1 | 1/2008 | Emanuel |
| 2008/0058588 A1 | 3/2008 | Emanuel |
| 2008/0058842 A1 | 3/2008 | Emanuel |
| 2008/0091074 A1 * | 4/2008 | Kumar ............... A61B 1/012 600/156 |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |

(56) References Cited

U.S. PATENT DOCUMENTS

| | | | |
|---|---|---|---|
| 2008/0249534 A1 | 10/2008 | Gruber et al. | |
| 2008/0249553 A1 | 10/2008 | Gruber et al. | |
| 2008/0262308 A1 | 10/2008 | Prestezog et al. | |
| 2008/0287961 A1* | 11/2008 | Miyamoto | A61B 17/3415 606/127 |
| 2009/0270812 A1 | 10/2009 | Litscher et al. | |
| 2009/0270895 A1 | 10/2009 | Churchill et al. | |
| 2009/0270896 A1 | 10/2009 | Sullivan et al. | |
| 2009/0270897 A1 | 10/2009 | Adams et al. | |
| 2009/0270898 A1 | 10/2009 | Chin et al. | |
| 2010/0087798 A1 | 4/2010 | Adams et al. | |
| 2010/0152647 A1 | 6/2010 | Shener et al. | |
| 2010/0198005 A1* | 8/2010 | Fox | A61B 17/3415 604/164.1 |
| 2010/0268023 A1* | 10/2010 | Campo | A61B 1/303 600/104 |
| 2012/0010464 A1* | 1/2012 | Adams | A61B 1/303 600/156 |
| 2012/0078038 A1* | 3/2012 | Sahney | A61B 1/018 600/104 |
| 2014/0378771 A1* | 12/2014 | St. Onge | A61B 1/0008 600/201 |
| 2015/0031951 A1* | 1/2015 | Furlong | A61B 1/00133 600/106 |
| 2015/0032024 A1* | 1/2015 | Furlong | A61B 1/015 600/566 |
| 2017/0215964 A1* | 8/2017 | Harrah | A61B 1/018 |

OTHER PUBLICATIONS

European Search Report dated Jan. 3, 2020 issued in corresponding EP Appln. No. 17803520.0.

Chinese Office Action dated Feb. 14, 2022 issued in corresponding CN Appln. No. 201780032337.2. (Summary only).

* cited by examiner

CONTINUOUS FLOW ENDOSCOPE

CROSS-REFERENCE TO RELATED APPLICATIONS

This application claims the benefit of, and priority to, U.S. Provisional Patent Application No. 62/341,908, filed on May 26, 2016, the entire contents of which are hereby incorporated herein by reference.

BACKGROUND

Various types of endoscopes may be employed for surgical and exploratory procedures, some of which may involve fluid inflow, outflow, or both depending upon the operation being performed. Depending upon the operation, there may be challenges to entry, access, or removal, or other challenges during and after the procedure, and the endoscope employed may need to adapt to these challenges by being configured for minimally invasive procedures or other procedures developed in response to those challenges.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a continuous flow endoscope device including an elongated tubular member, a first channel, a second channel, and an optics device. The elongated tubular member defines an interior. The first channel is disposed within the interior of the elongated tubular member. The second channel is disposed within the interior of the elongated tubular member and is configured to receive an instrument therein during a first portion of an operation. A lumen defined through the second channel is fluidly isolated from a lumen defined through the first channel. The optics device is disposed in a free space of the interior of the elongated tubular member. The free space is a space within the interior of the elongated tubular member not occupied by either the first channel or the second channel.

In an aspect of the present disclosure, the first channel is dedicated to fluid inflow and the second channel is dedicated to fluid outflow. Alternatively, the first channel may be dedicated to fluid outflow and the second channel dedicated to fluid inflow.

In another aspect of the present disclosure, the first channel defines a moon-shaped cross-sectional configuration. Additionally or alternatively, the second channel defines an elliptical cross-sectional configuration.

In yet another aspect of the present disclosure, the optics device is disposed within an oculiform region disposed within the interior of the elongated tubular member.

In still another aspect of the present disclosure, second channel is configured to operate without an instrument therein during a second portion of the operation. Further, the first and second channels may be configured to maintain continuous fluid flow during both the first and second portions of the operation.

In still yet another aspect of the present disclosure, the second channel is disposed within the first channel.

In an aspect of the present disclosure, the second channel is removable from the interior of the elongated tubular member.

Another continuous flow endoscope device provided in accordance with aspects of the present disclosure includes a first elongated tubular member defining an interior, a first channel disposed within the interior of the elongated tubular member, a second elongated tubular member defining a second channel therein, and an optics device. The second elongated tubular member is removably disposed within the interior of the first elongated tubular member. The second channel is configured to receive an instrument therein during a first portion of an operation. A lumen defined through the second channel is fluidly isolated from a lumen defined through the first channel. An optics device is disposed in a free space of the interior of the first elongated tubular member. The free space is a space within the interior of the first elongated tubular member not occupied by either the first channel or the second elongated tubular member.

In an aspect of the present disclosure, the first channel is dedicated to fluid inflow and the second channel is dedicated to fluid outflow. Alternatively, the first channel may be dedicated to fluid outflow and the second channel dedicated to fluid inflow.

In another aspect of the present disclosure, the first channel defines a moon-shaped cross-sectional configuration. Additionally or alternatively, the second channel defines an elliptical cross-sectional configuration.

In yet another aspect of the present disclosure, the optics device is disposed within an oculiform region disposed within the interior of the elongated tubular member.

In still another aspect of the present disclosure, second channel is configured to operate without an instrument therein during a second portion of the operation. Further, the first and second channels may be configured to maintain continuous fluid flow during both the first and second portions of the operation.

In still yet another aspect of the present disclosure, the second channel is disposed within the first channel.

In an aspect of the present disclosure, the second elongated tubular member is configured to releasably lock in engagement with the first elongated tubular member.

BRIEF DESCRIPTION OF THE DRAWINGS

The above and other aspects and features of the present disclosure will become more apparent in view of the following detailed description when taken in conjunction with the accompanying drawings, wherein.

DETAILED DESCRIPTION

Figure 1A:
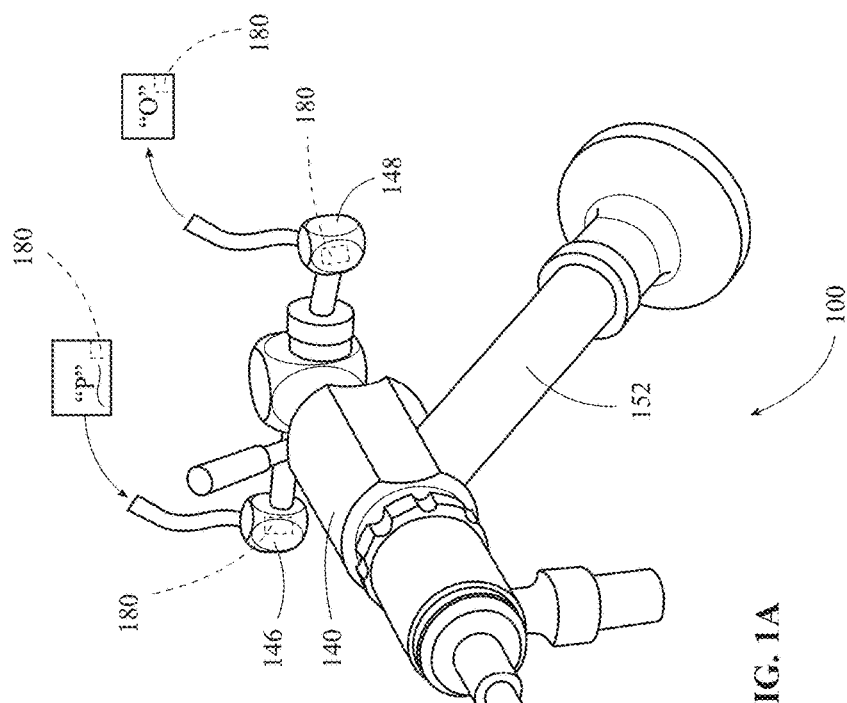
FIG. 1A is a perspective view of a surgical system provided in accordance with the present disclosure including a continuous flow endoscope device.

Medical endoscopes often contain channels in addition to their optical components in order to allow access for surgical instruments and fluid flow in and out of the operative field. In procedures conducted within a liquid environment, such as hysteroscopy, blood or other operative debris may cause impaired visualization. Visualization in a bloody or debris-filled liquid may be improved and maintained with continuous flow, because the constant circulation of fluid through the operative field continuously decreases the concentration of blood and/or debris. Continuous flow is achieved by providing separate pathways for fluid inflow and outflow from the operative field. In some cases, the addition of multiple channels within the endoscope creates a challenge with respect to maintaining an outer diameter of the endoscope small enough to provide atraumatic access to the operative field.

Endoscopes may be configured with a single channel shared by inflow and instrument access, and a removable outflow cannula which is inserted when there is no instrument in the channel. However, this configuration is not able to provide true continuous flow throughout the procedure.

In order to provide continuous flow as well as instrument access, endoscopes may be configured in a number of ways. For example, an endoscope may be provided with three channels, one each for instrument access, inflow, and outflow. An endoscope may alternatively be provided, as another example, with two channels, one for inflow and instrument access, and the other for outflow. As another example, an endoscope may be provided with a detachable outer sheath for outflow, wherein an outflow channel is created by the annular space between the outer surface of the endoscope and the inner surface of the sheath. Such an endoscope may further contain either two individual channels for inflow and instrument access or one shared channel for inflow and instrument access. Rather than providing a separate outflow channel and shared inflow and instrument access channel, this configuration may be reversed. That is, a separate inflow channel may be provided while the shared channel is utilized for outflow and instrument access.

In endoscope configurations where a dedicated channel and a shared channel are provided, when there is no instrument within the shared channel, there is significantly more cross-sectional area for flow in the shared channel than in the dedicated channel. As a result, the fluid resistance through the shared channel will be significantly less than through the dedicated channel. Since fluid flow rate is directly proportional to pressure difference and indirectly proportional to fluid resistance, it will take significantly greater pressure difference across the dedicated channel to achieve the same fluid flow rate as through the shared channel. If the shared channel is used for fluid outflow during a procedure, fluid will flow out of the operative field with much less resistance than into the operative field, and it will likely be difficult to keep the operative field filled. This is especially true in procedures such as hysteroscopy where the operative field is pressurized to distend tissue and create space. The significant pressure difference across the outflow channel would make sufficient fluid inflow and pressure control within the cavity highly difficult to achieve.

Figure 1B:
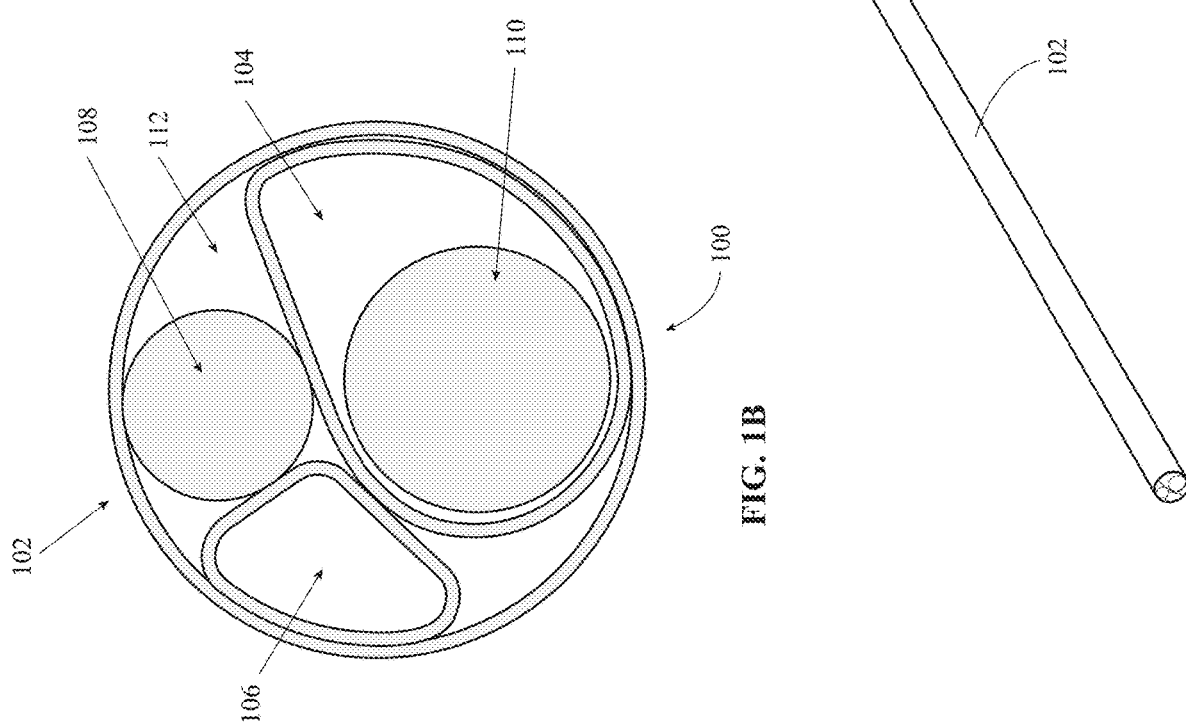
FIG. 1B is a transverse, cross-sectional view of the continuous flow endoscope of FIG. 1A.
Figure 2:
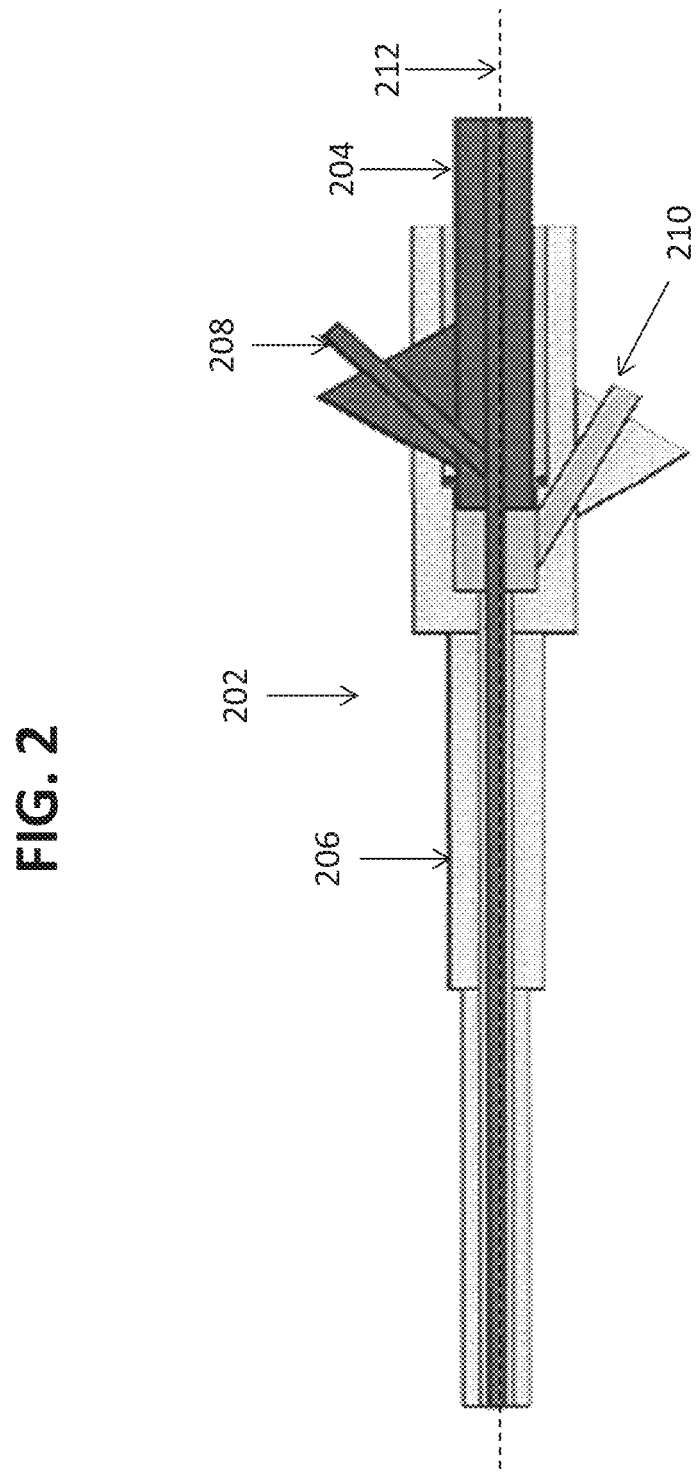
FIG. 2 is a longitudinal, cross-sectional view of another continuous flow endoscope device provided in accordance with aspects of the present disclosure, disposed in an assembled condition.
Figure 3:
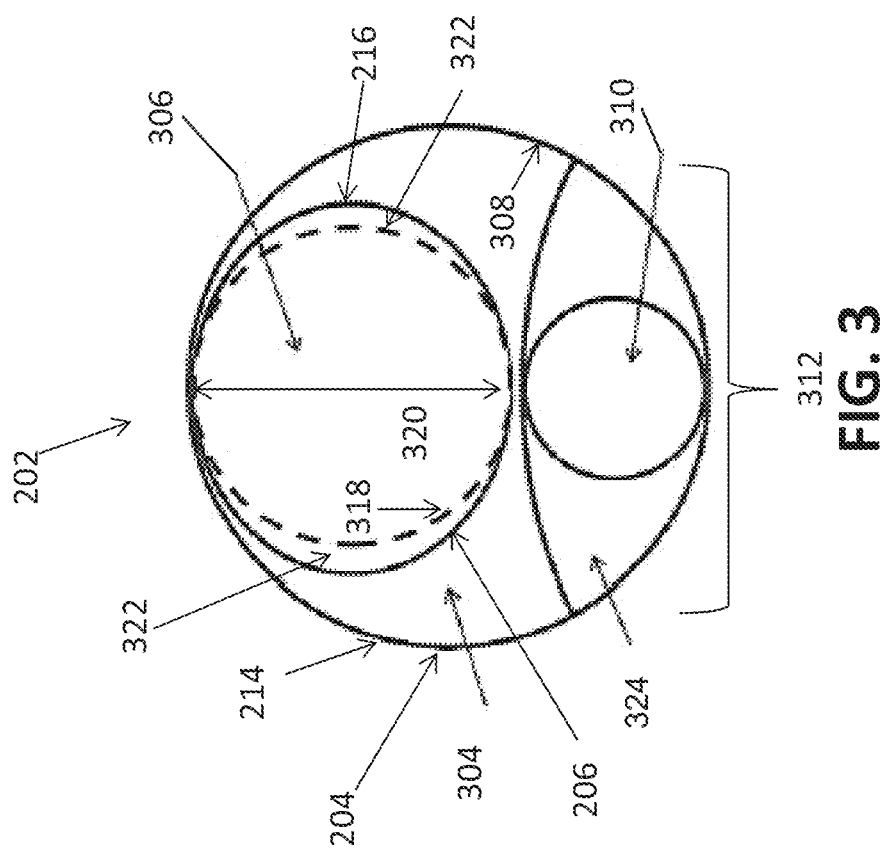
FIG. 3 is a transverse, cross-sectional view of the continuous flow endoscope of FIG. 2, disposed in the assembled condition.
Figure 4:
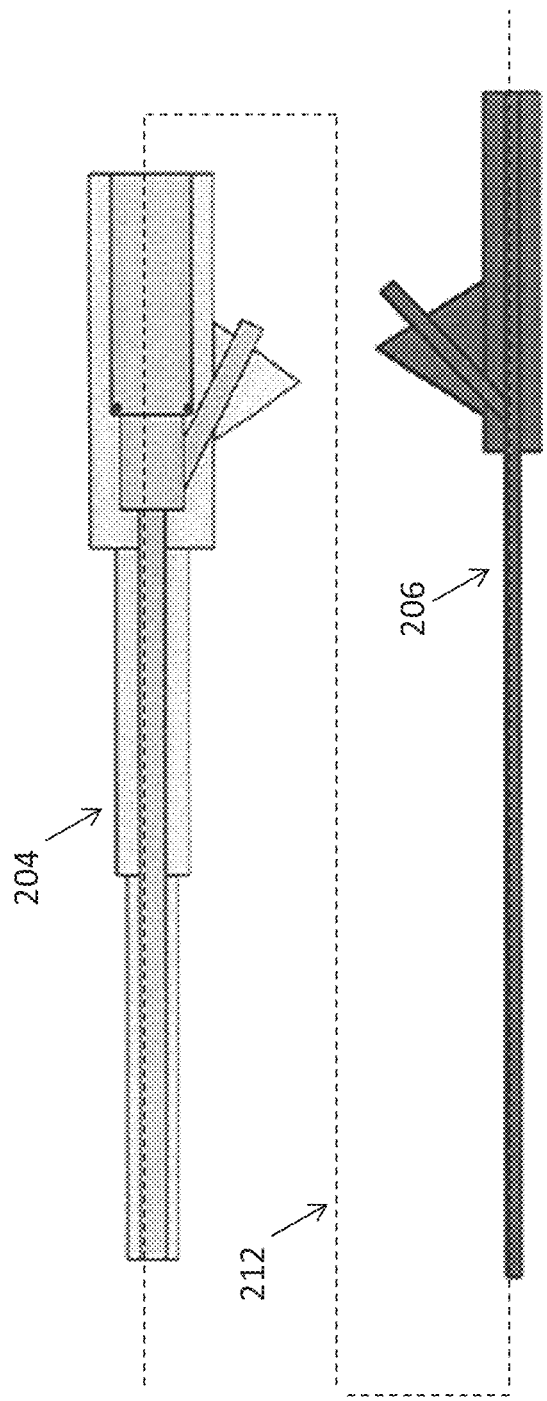
FIG. 4 is a longitudinal, cross-sectional view of the continuous flow endoscope of FIG. 2, disposed in a disassembled condition.
Figure 5:
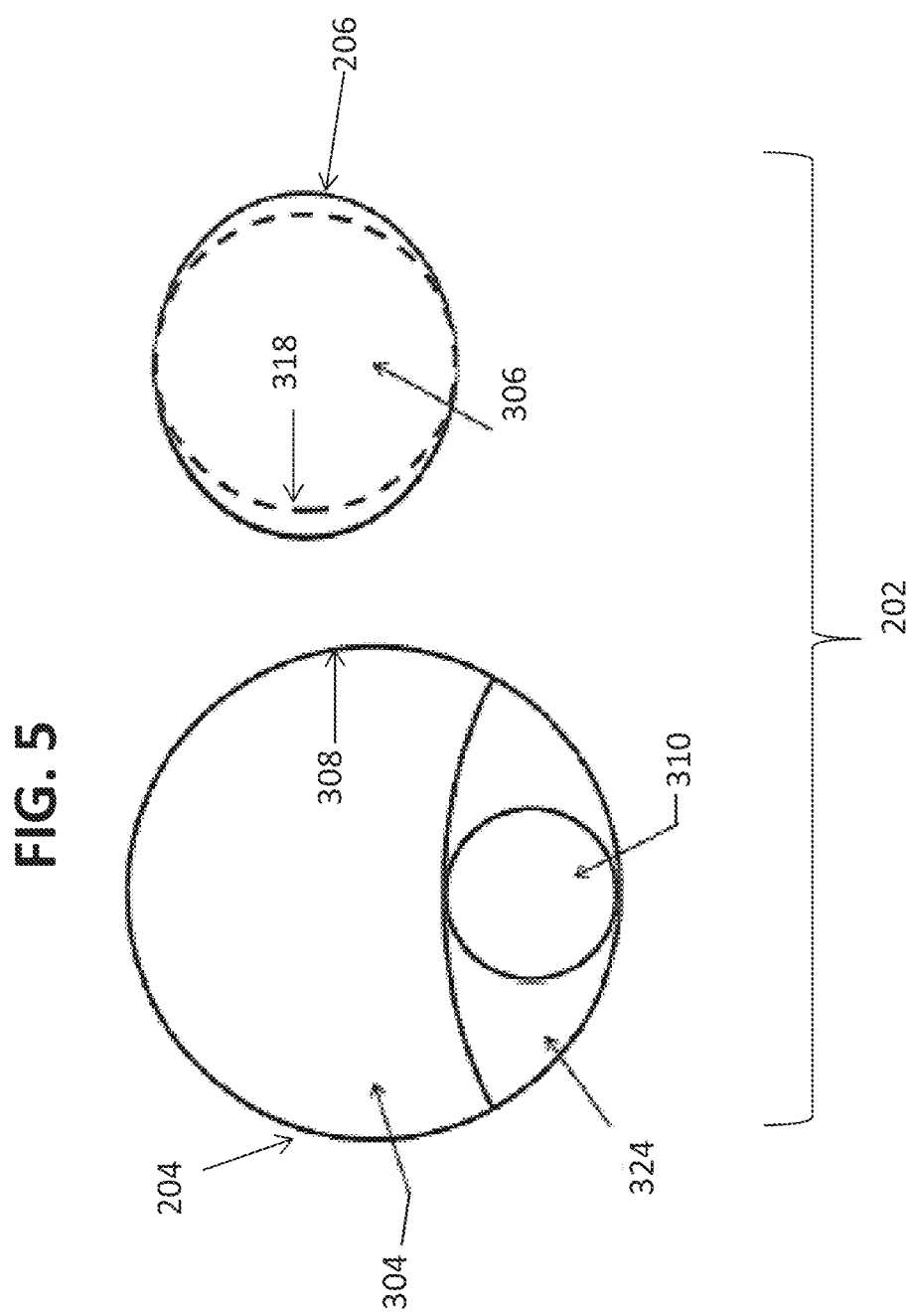
FIG. 5 is a transverse, cross-sectional view of the continuous flow endoscope device of FIG. 2, disposed in a disassembled condition.

Referring generally to FIGS. 1A and 1B, FIG. 1A is a perspective view of a continuous flow endoscope device 100 provided in accordance with the present disclosure. Continuous flow endoscope device 100 includes an elongated tubular member 102 and a proximal body 140. Proximal body 140 includes an inflow 146, an outflow 148, and an arm 152 that is connected to an imaging device (e.g., a camera) to capture images received via a visualization device, e.g., optics 108 (FIG. 1B), extending through elongated tubular member 102. Continuous flow endoscope device 100 forms a system in conjunction with pump "P" in communication with inflow 146 and/or an outflow reservoir "O" in communication with outflow 148. The system may be configured as an open system, wherein pump "P" and outflow reservoir "O" are separate, or may be a closed or partially-closed system, wherein outflow reservoir "O" is coupled to pump "P" or incorporated therein.

FIG. 1B is a transverse, cross-sectional view of the elongated tubular member 102 of continuous flow endoscope device 100 (FIG. 1A) including an instrument 110, e.g., a morcellator or other suitable surgical instrument, inserted therethrough. In some embodiments, elongated tubular member 102 defines a first channel 104 that is shared between fluid flow and instrument access, e.g., for instrument 110, and a second channel 106 for fluid flow as well. In some embodiments, the first channel 104 is shared between the instrument 110 and fluid outflow and, thus, is coupled to outflow 148 (FIG. 1A), while the second channel 106 is employed for fluid inflow and, thus, is coupled to inflow 146 (FIG. 1A). In other embodiments, the first channel 104 is shared between the instrument 110 and fluid inflow (and, thus, is coupled to inflow 146 (FIG. 1A)), while the second channel 106 is employed for fluid outflow (and, thus, is coupled to outflow 148 (FIG. 1)).

Optics 108 extend through elongated tubular member 102 within a free space 112 thereof that is outside of the first and second channels 104, 106, respectively. This free space 112 may constitute any portion of the interior lumen defined by elongated tubular member 102 other than the portions occupied by the first and second channels 104, 106, respectively.

Referring still to FIGS. 1A and 1B, in embodiments of the present disclosure, the first and the second channels 104, 106, respectively, of the elongated tubular member 102 of continuous flow endoscope device 100 are configured both individually and relatively such that fluid resistance through the first channel 104 does not decrease to a level significantly lower than the fluid resistance through the second channel 106, regardless of whether an instrument 110 is inserted through first channel 104. "Significantly lower" and "significantly similar" as utilized herein may refer to when fluid flow through the first channel 104 is within a predetermined range of the fluid flow through the second channel 106. Other components of continuous flow endoscope 100 and/or the system including the same are additionally or alternatively configured to maintain a substantially similar resistance between the first and second channels 104, 106, respectively, thus keeping the fluid flow between the channels 104, 106 substantially similar (within a predetermined range of each other).

In some embodiments, the cross-sectional areas accessible by fluid flow in both the first and second channels 104, 106, respectively, are relatively similar (with or without an instrument 110 inserted through one of the channels 104, 106). As a result, the fluid resistances created by the configuration of the first and second channels 104, 106, respectively, are substantially similar. The elongated tubular member 102 of continuous flow endoscope device 100 may include a variety of channel configurations and profile shapes, which allows for true continuous flow with or without an instrument 110 placed in the first channel 104, regardless of whether the first channel 104 is used for fluid outflow or fluid inflow. The determination as to whether the first channel 104 is used for fluid inflow or fluid outflow may be based on the type of procedure being performed, the patient, the involved medical professionals, and other factors that may impact the type and size of instrument(s) 110 employed in the procedure so that when the instrument(s) 110 are removed/replaced, fluid resistance is maintained between the first and second channels 104, 106, respectively.

The first and second channels 104, 106, respectively, may be configured to be different sizes and/or shapes (geometries), and may be permanently fixed within elongated tubular member 102. The elongated tubular member 102 also accommodates the optics device 108 while true continuous fluid flow is occurring in the first and second channels 104, 106, respectively, regardless of whether an instrument 110 is present in the first channel 104 or the second channel 106. The first channel 104 and/or the second channel 106 may taper the diameter of their respective cross-sections along the length of the elongated tubular member 102 in the proximal-to-distal direction. The first and second channels 104, 106, respectively, are not in communication with each other, e.g., are separate from one another. Further, no sheath is required for use with continuous flow endoscope device 100.

The cross-section of the channel shared between fluid flow and instrument access, e.g., first channel 104, has an inner diameter greater than the outer diameter of instruments, e.g., instrument 110, inserted therethrough in order to enable flow in the resulting annular space. This shared channel 104 may also have a cross-section shaped differently from the outer profile of the instrument 110 in order to create additional space for fluid flow. As illustrated in FIG. 1B, the cross-section of the shared channel 104 may, more specifically, include a portion that complements the outer profile of the instrument 110 and another portion that does not, e.g., extends away from, the outer profile of the instrument 110 to create the additional space for fluid flow.

The first and second channels 104, 106, respectively, may define a cross-sectional geometry of a circle, polygon, polygon with rounded edges, kidney, bean, teardrop, half-moon, triangle, and combinations thereof. The first and second channels 104, 106, respectively, may define different cross-sectional geometries or similar geometries, or similar geometries with different relative scales. The channels 104, 106 may be formed from rigid or semi-rigid biocompatible material and, as noted above, are disposed within the elongated tubular member 102 of continuous flow endoscope device 100 without the aid of a sheath.

Instruments 110 used in conjunction with continuous flow endoscope device 100 may be relatively large and take up a significant portion of the cross-section of the lumen of elongated tubular member 102 of continuous flow endoscope device 100 when inserted through first channel 104. As a result, the first channel 104 may be relatively large and, together with the optics 108, may leave little space remaining for the second channel 106, which is, as a result, relatively small when compared with the first channel 104. When an instrument 110 is placed within the first channel 104, regardless of whether the first channel 104 is used for inflow or outflow, the cross-sectional areas accessible by fluid flow in both the first and second channels 104, 106 are substantially similar, so the fluid resistance of the first and second channels 104, 106 are similar, for example, when the length of the first channel 104 and the length of the second channel 106 are substantially similar (within a predetermined range of each other).

In some embodiments, the substantially similar resistance in the first and second channels 104, 106 may be achieved and/or maintained by an automatic, manual, electrical, mechanical, or electro-mechanical fluid control mechanism 180 of the pump "P" and/or the outflow reservoir "O." Thus, the presence or absence of an instrument 110 within first channel 104 can be accounted for (or further accounted for).

In embodiments, the first channel 104 is used for fluid inflow and, thus, the fluid resistance of the second channel 106 (that has a smaller cross-section than the first channel 104) will be higher, allowing the operative field to remain pressurized. In embodiments where the first channel 104 is used for fluid inflow during a procedure, the fluid resistance of the fluid inflow will change throughout the procedure as instruments 110 are inserted into and removed from continuous flow endoscope device 100, since various instruments 110 may be employed throughout a procedure. In embodiments where continuous flow endoscope device 100 is used in combination with an external fluid control pump "P" (incorporating a fluid control mechanism 180 therein), the pump "P" will regulate the fluid inflow supply pressure in the first channel 104 in order to control the fluid pressure inside the operative space (e.g., the body cavity). In order to more accurately control pressure, the external fluid control pump "P" may employ the resistance of the fluid inflow path to calculate the theoretical pressure at the distal end of the elongated tubular member 102 of continuous flow endoscope device 100.

In some embodiments, the design of the channels 104, 106 may be sufficient to maintain the resistance of fluid flow. In some embodiments, if this measured resistance changes during the procedure and exceeds a predetermined amount, the fluid control mechanism 180 of the pump "P" is utilized to maintain the substantially similar resistances of fluid flow to control the pressure within the operative field to a desired accuracy. In some embodiments, the fluid control mechanism 180 of the pump "P" is not capable of maintaining such resistances. In these embodiments, an additional feature, such as another fluid control mechanism 180 associated with the outflow reservoir "O" coupled to the outflow 148, may be employed additionally or alternatively to maintain the fluid resistance of the fluid inflow path at a constant value.

In some embodiments, the first channel 104 is used for outflow, and the fluid resistance of the second (inflow) channel 106 does not change during the procedure, allowing the pump "P" to accurately control pressure because of the design of the respective channels 104, 106.

FIGS. 2-5 illustrate another continuous flow endoscope 202 provided in accordance with the present disclosure. Continuous flow endoscope 202 is shown in an assembled condition in FIGS. 2 and 3 and in a disassembled condition in FIGS. 4 and 5. Except as specifically contradicted below, continuous flow endoscope 202 may be configured similarly as continuous flow endoscope 100 (FIGS. 1A and 1B), may include any of the features thereof, and/or may form a system similarly as continuous flow endoscope 100 (FIGS. 1A and 1B), e.g., in conjunction with pump "P" and/or an outflow reservoir "O" (see FIG. 1A). In embodiments, continuous flow endoscope 202 differs from continuous flow endoscope 100 (FIGS. 1A and 1B) in that continuous flow endoscope 202 is configured for disassembly (into first and second subassemblies 204, 206) and in the arrangement of the internal features thereof, as detailed below.

Continuous flow endoscope device 202 includes a first subassembly 204 and a second subassembly 206 telescopically insertable into and removable from first assembly 204 along a shared central axis 212. First subassembly 204 includes an elongated tubular body having a first channel 304 and a plurality of optical components 310 disposed within an interior thereof, and may contain a fluid port 208. Second subassembly 206 includes an elongated tubular body having a second channel 306 of continuous flow endoscope device 202 disposed within an interior thereof and may contain one or more fluid ports 210. Alternatively, second subassembly 206 may including both fluid ports 208, 210.

Continuous flow endoscope device 202 allows for a variety of geometries, including those with corner-like or sharp transitions in channel cross-sections, to be employed, since first subassembly 204 and second subassembly 206 may be disassembled to facilitate cleaning and sterilization. Continuous flow endoscope device 202 is operational when the subassemblies 204, 206 are assembled, but not when they are disassembled. When continuous flow endoscope device 202 is in the assembled condition, a plurality of mating features (not explicitly shown) on first and second subassemblies 204, 206, respectively, are configured to lock second subassembly 206 relative to first subassembly 204. In some embodiments, the mating features (not explicitly shown) may include a single-button (single-digit) release mechanism that may include spring latch functionality. In addition, lead-in features (not explicitly shown) on the first and second subassemblies 204, 206, respectively, may be provided to align and guide the second subassembly 206 into the first subassembly 204 to prevent wedging or jamming during assembly.

First channel 304 of first subassembly 204 occupies an area within the interior of the elongated tubular member of first subassembly 204. More specifically, first channel 304 occupies a space which may be defined by inner surface 308 of the elongated tubular member of first subassembly 204 and is fluidly isolated from the plurality of optics components 310. Optics components 310 are located within an oculiform region 312 of the elongated tubular member of first subassembly 204 between a portion of inner surface 308 of the elongated tubular member of first subassembly 204 and an interior wall that fluidly isolates oculiform region 312 from first channel 304. First channel 304 may be used for fluid inflow. A second channel 306 disposed within the elongated tubular member of second subassembly 206 may be configured to accommodate a wide range of instruments 318, and may be used for fluid outflow. When second subassembly 206 is disposed within the elongated tubular member of first subassembly 204, the second channel 306 of second subassembly 206 is thus likewise disposed within and occupies a portion of the interior of the elongated tubular member of first subassembly 204. In some embodiments, a throttle feature (not shown) is disposed within the fluid outflow path to increase fluid resistance when an instrument 318 is not disposed within the second channel 306.

Optical components 310 are constrained within an oculiform region 312 at the bottom of the cross-section of the elongated tubular member of first subassembly 204. Optical components 310 may include but are not limited to a rod lens system, coherent fiber optic bundle, miniature camera components, illumination fibers, or LED light components. In an embodiment, a plurality of illumination fibers (light) 324 are located on either side of the optical components 310 within oculiform region 312. First channel 304 occupies the remaining space within the boundary of the cross-section of the elongated tubular member of first subassembly 204, resulting in a moon-shaped first channel 304.

In an embodiment, second channel 306 disposed within the elongated tubular member of second subassembly 206 may be defined at least in part by an elliptical cross-section of the elongated tubular member thereof, with a minor diameter 320 such that second subassembly 206 fits within first channel 304 of first subassembly 204 when the minor diameter 320 is oriented to extend between oculiform region 312 and an opposed portion of inner surface 308 of first subassembly 204. The minor diameter 320 of second channel 306 is such that an instrument 318 may be inserted through second channel 306, and, when a circular instrument is inserted, the instrument 318 may fully occupy the minor diameter 320 of second channel 306. It is appreciated that, in other embodiments, instruments defined in whole or in part by a cross-section or cross-sections that are not circular may also fully occupy the minor inner diameter 320. In an embodiment, additional space 322 remains within the second channel 306 on either side of the instrument 318, e.g., along the major diameter thereof, to allow for fluid outflow, e.g., true continuous flow, for the duration of the procedure. In an embodiment, when instrument 318 is removed from the second channel 306, continuous flow is maintained even if another instrument is not inserted in the second channel 306.

Continuous flow endoscope device 202 achieves continuous flow both with and without an instrument 318 therein and maximizes use of space within the endoscope cross-section. In particular, use of space is maximized because the optical components 310, channels 304, 306, and structural elements 204, 206 occupy 100% of the cross-sectional area of the working section, e.g., the interior area defined by the elongated tubular member of the first subassembly 204. This space-use efficiency allows for equivalent or better fluid performance at a reduced outer dimension for less traumatic access. In addition, the fluid resistance to inflow does not measurably vary during a procedure, allowing for better cavity pressure control when used with a fluid pump system, and disassembly allows for improved ability for cleaning and sterilization, thereby enhancing patient safety.

Figure 6:
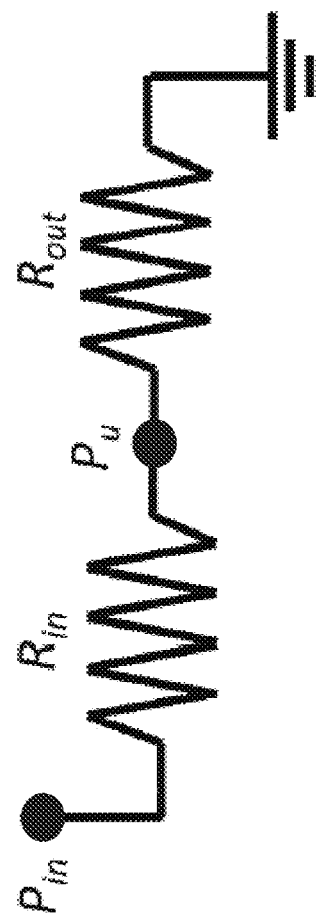
FIG. 6 is a schematic representation illustrating a fluid circuit of a continuous flow endoscope device modeled on a first-order basis as two resistors in series.

FIG. 6 represents a fluid circuit of an endoscope modeled on a first-order basis as two resistors in series. The first resistor, Rin, is the fluid impedance of the inflow channel, and the second resistor Rout is the fluid impedance of the outflow channel. The point between the resistors Rin and Rout represents the pressure within the cavity or organ Pu. In a steady flow state, the cavity pressure Pu remains constant, and the flow rates Rin and Rout are equal. Pressure supplied to the scope at the inflow Rin is indicated as Pin and the outflow pressure is assumed to be zero, or ground.

The ability of fluid to clear the visual field may be dependent upon the fluid flow rate in and out of the cavity, which is equal in a steady flow state. See Equation (1):

$$Q = \frac{P_{in}}{(R_{in} + R_{out})} \tag{1}$$

The flow rate depends upon the fluid impedances of both the inflow and outflow channels; an increase will result in a decrease in flow rate and subsequently a decrease in ability to clear the visual field. As such, general cross-sectional areas of both the inflow and outflow may be increased (to increase their combined resistance) in order to achieve sufficient (usable) overall flow rate.

The ability to maintain distension of the organ or cavity depends on the pressure in the cavity. In the series-resistor model, with the outflow connected to ground (as opposed to vacuum), the overall pressure difference across the scope is equal to the inflow pressure supplied to the scope, given in Equation (2):

$$P_{in} = Q \cdot (R_{in} + R_{out}) \quad (2)$$

The cavity pressure is given in Equation (3):

$$P_u = Q \cdot (R_{out}) \quad (3)$$

Substitution results in the Equation (4), an expression for cavity pressure as a function of inflow pressure and fluid channel resistances:

$$P_u = P_{in} \left( \frac{R_{out}}{R_{in} + R_{out}} \right) \quad (4)$$

Theoretically, it is always possible to increase the inflow pressure in order to increase the cavity pressure. However, there are practical limits on the inflow pressure: a fluid bag may only be hung so high in an operating room and fluid pumps have safety limits on inflow pressure. As such, it is desirable to maintain the cavity pressure as close as possible to the inflow pressure in order to provide sufficient distension. This is accomplished by maximizing the resistance of the outflow with respect to the resistance of the inflow, as provided in Equation (5):

$$\lim_{\frac{R_{out}}{R_{in}} \to \infty} P_u = \lim_{\frac{R_{out}}{R_{in}} \to \infty} P_{in} \left( \frac{R_{out}}{R_{in} + R_{out}} \right) = P_{in} \quad (5)$$

As such, in order to increase the fluid performance of the endoscope: the sum of the fluid resistances of the inflow and outflow should be decreased to increase fluid flow rate (ability to clear visual field); the ratio of the outflow fluid resistance to the inflow fluid resistance should be increased to keep the cavity pressure as close as possible to the inflow pressure (maintain distension); and any instruments inserted through the endoscope which provide an additional outflow path should also be considered.

Decreasing fluid resistance may be achieved by increasing the cross-sectional area available for fluid flow. As such, a primary challenge in continuous flow endoscope design is to provide sufficient cross-sectional area for fluid flow within an endoscope outer diameter that is small enough to allow atraumatic access to the operative field. The above-detailed embodiments overcome these challenges.

While exemplary embodiments have been shown and described, modifications thereof can be made by one skilled in the art without departing from the scope or teachings herein. The embodiments described herein are exemplary only and are not limiting. Many variations and modifications are possible and are within the scope of the present disclosure. Accordingly, the scope of protection is not limited to the exemplary embodiments described herein, but is only limited by the claims that follow, the scope of which shall include all equivalents of the subject matter of the claims. Unless expressly stated otherwise, the steps in a method claim may be performed in any order.

What is claimed is:

1. A continuous flow endoscope device comprising:
   an elongated tubular member defining a lumen and a longitudinal axis;
   a first channel disposed within the lumen of the elongated tubular member, the first channel defining a first cross-sectional area substantially perpendicular to the longitudinal axis;
   a second channel disposed within the lumen of the elongated tubular member externally of and separately from the first channel, the second channel configured to receive an instrument having a circular cross-section during a first portion of an operation, the second channel defining a second cross-sectional area substantially perpendicular to the longitudinal axis, wherein the second cross-sectional area of the second channel is different from the first cross-sectional area of the first channel, and wherein the second cross-sectional area of the second channel includes a first portion configured to complement the circular cross-section of the instrument and a second portion that extends away from the circular cross-section of the instrument such that, with the instrument inserted through the second channel, the second portion of the second cross-sectional area defines additional space not occupied by the instrument; and
   an optics device disposed in a first free space of the lumen of the elongated tubular member, the first free space being a space within the lumen of the elongated tubular member not occupied by either the first channel or the second channel,
   wherein the lumen of the elongated tubular member defines a second free space, the second free space separated from the first free space by the first and second channels and being a space within the lumen of the elongated tubular member not occupied by either the first channel or the second channel,
   wherein the first channel is arranged to pass a fluid in a first direction and the second channel is arranged, with the instrument inserted through the second channel, to pass the fluid through the additional space in a second direction different from the first direction, the first and second channels arranged to isolate the fluid from the first free space of the lumen of the elongated tubular member.

2. The continuous flow endoscope device according to claim 1, wherein the first channel is dedicated to fluid inflow and the second channel is dedicated to fluid outflow.

3. The continuous flow endoscope device according to claim 1, wherein the first channel is dedicated to fluid outflow and the second channel is dedicated to fluid inflow.

4. The continuous flow endoscope device according to claim 1, wherein the second channel is configured to operate without an instrument therein during a second portion of the operation.

5. The continuous flow endoscope device according to claim 4, wherein the first and second channels are configured to maintain continuous fluid flow during both the first and second portions of the operation.

6. The continuous flow endoscope device according to claim 1, wherein the second channel is removable from the interior of the elongated tubular member.

7. The continuous flow endoscope device according to claim 1, wherein the optics device is configured to be removably received in the first free space of the lumen of the elongated tubular member.

8. The continuous flow endoscope device according to claim 1, wherein a shape of the second cross-sectional area is different from a shape of the first cross-sectional area.

9. The continuous flow endoscope device according to claim 1, wherein the instrument is configured to be removably received in the second channel.

10. The continuous flow endoscope device according to claim 1, wherein the first and second free spaces define different cross-sectional shapes.

11. The continuous flow endoscope device according to claim 1, wherein each of the first and second free spaces is defined by portions of the elongated tubular member, the first channel, and the second channel.

* * * * *